United States Patent [19]

Fraden

[11] Patent Number: 4,509,527
[45] Date of Patent: Apr. 9, 1985

[54] CARDIO-RESPIRATION TRANSDUCER

[75] Inventor: Jacob Fraden, Hamden, Conn.

[73] Assignee: Timex Medical Products Corporation, Waterbury, Conn.

[21] Appl. No.: 483,358

[22] Filed: Apr. 8, 1983

[51] Int. Cl.³ ............................................. A61B 5/10
[52] U.S. Cl. .................................. 128/671; 128/721; 128/774
[58] Field of Search .............................. 128/670–671, 128/721–722, 774, 782; 340/573, 666; 307/400

[56] References Cited

U.S. PATENT DOCUMENTS

| 3,760,794 | 9/1973 | Basham | 340/573 X |
| 3,836,900 | 9/1974 | Mansfield | 128/671 |
| 4,066,072 | 1/1978 | Cummins | 128/671 X |
| 4,250,415 | 2/1981 | Lewiner et al. | 307/400 |
| 4,320,766 | 3/1982 | Alihanka et al. | 128/671 |
| 4,366,810 | 1/1983 | Slanetz, Jr. | 340/573 X |
| 4,438,771 | 3/1984 | Friesen et al. | 128/671 |

FOREIGN PATENT DOCUMENTS 2605809  8/1977  Fed. Rep. of Germany ...... 307/400

Primary Examiner—Lee S. Cohen
Assistant Examiner—Angela D. Sykes
Attorney, Agent, or Firm—William C. Crutcher

[57] ABSTRACT

A laminated, sheet-like transducer is disclosed which produces an output signal in response to changing mechanical forces applied thereto. The transducer includes a top flexible plate with a matrix of uniformly spaced-apart convex members on one surface and a bottom flexible plate with a matrix of uniformly spaced-apart convex members on one surface. The convex members on the surface of one plate are aligned with the spaces between the convex members on the surface of the other plate. A synthetic resin polymer electret film is sandwiched between the convex members of each plate and becomes deformed when the convex members press against and horizontally stretch the electret film due to the changing mechanical forces applied to the transducer. Electrodes are connected to opposite surfaces of the electret film and form, at least on one surface, a uniformly spaced-apart electrically interconnected electrode configuration. The electrodes sense the electrical charges in the electret film and produce a signal proportional to the magnitude of the changing mechanical forces which induce the electrical charges.

23 Claims, 6 Drawing Figures

CARDIO-RESPIRATION TRANSDUCER

BACKGROUND OF THE INVENTION

This invention relates to piezoelectric transducers that are responsive to changing mechanical forces applied thereto. The changing mechanical forces may be produced by respiratory or cardiac activity of patients.

The piezoelectric transducer is made of material which produces an electrical charge that is proportional to the degree of strain in the piezoelectric material due to the motion of a mass exerting a force thereon. An electrical potential develops along certain crystallographic lattice axes of the material in response to movement of charge as a result of mechanical deformation of the material. The crystal lattice structure of the material is physically deformed by application of an increasing force caused by the moving mass. The deformation of the lattice produces a relative displacement of the positive and negative charges within the crystal lattice internal to the material. The displacement of the internal charges produce equal external charges of opposite polarity on the opposite surfaces of the material creating the "piezoelectric effect". The charges may be measured by applying metal contacts or electrodes to the opposite surfaces of the piezoelectric material and measuring the potential difference between them. The magnitude and polarity of the induced surface charges are proportional to the magnitude and direction of the applied force, produced by the moving mass, as given by:

$$Q(\text{coulombs}) = d(\text{coulomb/m}^2/\text{newton/m}^2) F(\text{newtons/m}^2)$$

where Q is the surface charge, d is the piezoelectric constant and F is the applied force.

The piezoelectric transducer may be considered electrically equivalent to a charge generator, delivering a charge proportional to the force applied to the piezoelectric material. The piezoelectric transducer may be connected to a charge-to-voltage converter so that the electrical charge provided to the converter is proportional to the rate of change of the force applied or deformation of the transducer.

It is possible to induce the "piezoelectric effect" in certain synthetic resin polymers (organic compounds) by cooling them from a liquid or soft state to the solid state in the presence of an electric field or by polymerization in the presence of an electric field. Typical materials used to make such piezoelectric transducers (electret transducers) are beeswax and polymers such as polyvinylidene fluoride. For example, U.S. Pat. No. 3,792,204 issued to Murayana et al. shows a transducer composed of a piezoelectric film of a polyvinylidene fluoride resin having electroconductive material on the opposite surfaces of the film. The molecules of the film are oriented by stretching the film. The "piezoelectric effect" is produced when a force is applied perpendicular to the plane of the film causing deformation of the film parallel to the direction of molecular orientation. The transducer uses the electret of a vinylidene fluoride resin film as a vibrator or oscillator to provide for an acoustic transducer, U.S. Pat. No. 3,996,922, which is a divisional of U.S. Pat. No. 3,898,981, issued to Basham shows a force responsive transducer that senses changes due to reciprocating forces and motions caused by respiration or heart rate. The force responsive electret transducer has movable parts adapted for placement beneath a patient or a patient support such as a mattress. There is no direct attachment of the transducer to the patient. The protective covering material for the transducer is vinyl, the electrodes attached to the electret material are flexible steel sheets and the electret film is Teflon. The normal breathing motion of the patient produces a varying applied force against the electrodes. The increasing force causes the electrodes to be moved nearer the electrically polarized film in a manner similar to moving a conductor through an electric field such that a current flows through a conductor connecting the electrodes to electronic circuitry. The current flow in the conductor varies with the force applied to the electrode which, in turn, varies with the patient's respiration rate.

With the application of a high (polarizing) voltage to produce the electric fields for inducing the "piezoelectric effect" in suitable materials, there is a reorientation of the crystalline structure which persists after removal of the polarizing voltage. Often this induction process is carried out at an elevated temperature. This technique, in addition to producing a material with a high piezoelectric constant, removes the geometrical constraints of crystallographic axes and makes it possible to cast piezoelectric materials in any desired form.

A piezoelectric material need be distorted only a small amount to obtain a voltage in the fractional volt range. For this reason, piezolectric material may be considered as efficient isometric transducers. The stiffness of piezoelectric materials is usually high, and the permissible deformations are small. For example, the deformation of the crystal material used in phonograph pickups is ten (10) microns per gram of weight.

An output voltage cannot be maintained by the piezoelectric material when a sustained force is applied. Therefore, piezoelectric material is generally suited to the measurement of changing mechanical forces. Piezoelectric material can produce an output voltage for changes in mechanical deformation having a frequency of a few Hertz to many megaHertz. The upper frequency limit is determined by the total mass and stiffness of the moving transducer.

U.S. Pat. No. 4,144,877 issued to Frei et al. shows piezoelectric electret transducers made of organic compounds which are formed by cooling from the liquid or soft state to the solid state in the presence of an electric field or by polymerization in the presence of an electric field. Typical materials used to make electrets or beeswax and polymers such as polyvinylidene fluoride. Conducting electrodes are deposited on the electret material by known means and can be in an array configuration.

U.S. Pat. No. 4,204,135 issued to Murayana shows organic piezoelectric elements in which the shifting of the piezoelectric modulus by the influence of stretching conditions is not as large for an unoriented vinylidene fluoride copolymer as for a vinylidene fluoride homopolymer.

Other pertinent patents include U.S. Pat. No. 3,820,529 issued to Gause et al. and U.S. Pat. No. 4,299,233 issued to Lemelson.

It is an object of this invention to monitor both respiratory and cardiac activity of a patient using a transducer with a synthetic resin polymer electret.

An object of this invention is to provide a transducer, responsive to changing mechanical forces, that operates in a relatively low frequency bandwidth.

Another object of this invention is to provide for a transducer having both high sensitivity to changing mechanical forces and noise immunity.

Other objects of the invention include providing a transducer that is not connected directly to the patient, that is easy to use and that can be adapted for use by adults as well as children and that gives an accurate indication of both heart and respiratory activity regardless of the patient's position on the transducer.

SUMMARY OF THE INVENTION

A laminated, sheet-like transducer is disclosed which is electrically connected to electronic circuit means and responsive to changing mechanical forces applied thereto. The transducer comprises a top flexible plate including a first surface having a matrix of uniformly spaced-apart first convex members and a bottom flexible plate including a second surface with a matrix of uniformly spaced-apart second convex members aligned with the spaces between the first convex members. An electret film made of a synthetic resin polymer is sandwiched between the first and second surfaces of the top and bottom plates whereby the electret film produces electrical charges when deformed due to the first and second convex members pressing against and horizontally stretching the electret film in response to the changing mechanical forces. Electrodes are attached to opposite surfaces of the electret film and form, at least on one surface, a uniformly spaced-apart electrically interconnected electrode configuration, whereby the electrodes sense the electrical charges to produce a signal transmitted to the electronic circuit means which is proportional to the magnitude of the changing mechanical forces.

DESCRIPTION OF THE PREFERRED EMBODIMENTS

Figure 1:
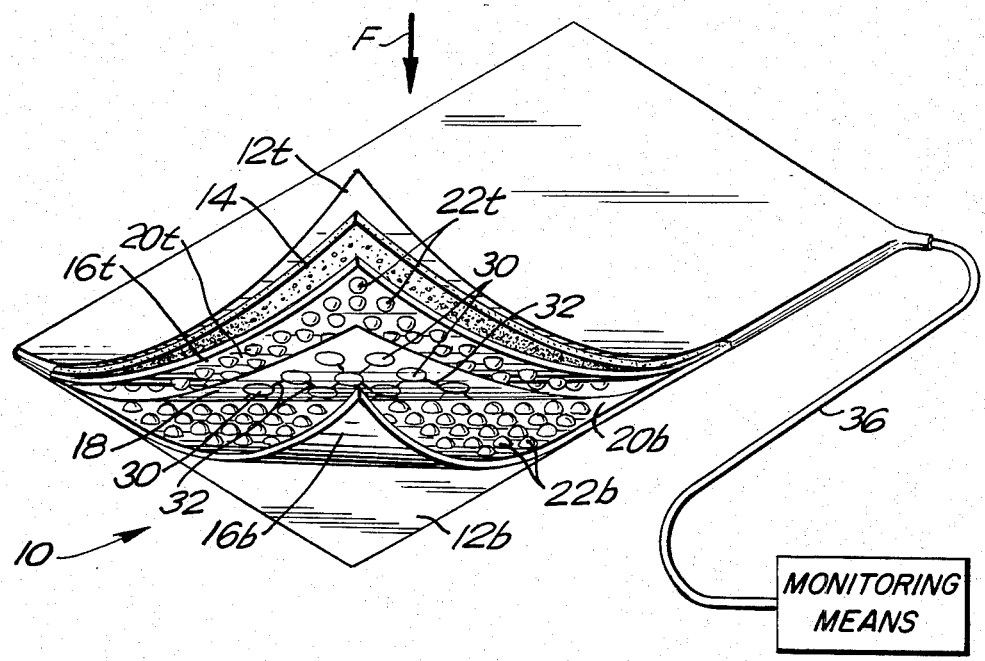
FIG. 1 is a perspective view of the sheet-like, laminated transducer of the invention with portions thereof separated to show the laminations.

As shown in FIG. 1, sheet-like, laminated transducer 10 includes top and bottom protective layers 12$t$ and 12$b$, foam padding 14, top and bottom resilient plates 16$t$ and 16$b$ and piezoelectric material 18 having electrically interconnected metalized surfaces thereon.

Specifically, transducer 10 may be predeterminedly positioned with respect to a patient in order to respond to the patient's heart rate and respiration rate. Because of this use, transducer 10 may be referred to as a cardiorespiratory transducer. The transducer is adapted for placement between a patient and a patient support, such as a mattress, for sensing changes in the mechanical forces caused by the patient's cardiac and respiratory activity and may be used as an integral part of an apnea detecting system. The sheet-like transducer may be made to fit the size of any mattress in order to be responsive to the substantially vertical, cyclical motions transmitted to the transducer by the patient's heart beat and respiration regardless of the patient's position on the mattress. Furthermore, the transducer does not come into direct contact with the patient's body and is not adapted for application to any part of the patient's body.

Top and bottom protective layers, 12$t$ and 12$b$, may be made of an elastic vinyl material bonded together at the edges to enclose the other components of laminated cardiorespiratory transducer 10 for providing protection against moisture and wear and tear due to normal use.

Foam padding 14 is made of dense polyurethane foam and provides for a uniform distribution of the changing mechanical force (F) which is applied to the transducer as indicated by the arrow in FIG. 1.

Top and bottom resilient, flexible plates, 16$t$ and 16$b$, are made of air-filled polyethylene. On first surface 20$t$ of top resilient plate 16$t$ are a plurality of uniformly spaced-apart first convex members 22$t$ forming a matrix thereon. On second surface 20$b$ of bottom resilient plate 16$b$ are a plurality of uniformly space-apart second convex members 22$b$ forming a matrix thereon. First and second surfaces, 20$t$ and 20$b$, of top and bottom plates 16$t$ and 16$b$ are proximal to one another.

Piezoelectric material 18 (an electret) is a polarized film made of polyvinylidene fluoride (PVDF). The PVDF film carries a permanent electrical polarization or voltage between opposing surfaces thereof. As a result, one surface of the film has a positive polarity and the opposite surface has a negative polarity thereby producing an electric field across the film. Piezoelectric material 18 has attached thereto on both surfaces metalized areas which will be discussed below.

Figure 2:
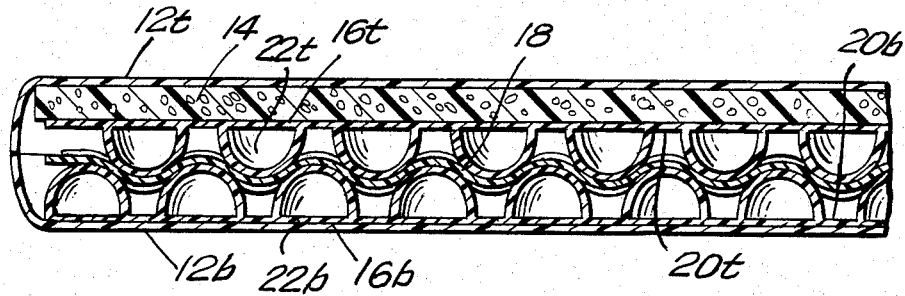
FIG. 2 is a cross-sectional view of the transducer of FIG. 1.

For this invention, the laminated, sheet-like cardiorespiratory transducer has the structure shown in FIG. 2. Piezoelectric material 18 is sandwiched between first and second surfaces, 20$t$ and 20$b$, of top and bottom resilient plates, 16$t$ and 16$b$. The convex members on the surface of one plate are in alignment with the spaces between convex members on the surface of the other plate. Foam padding 14 is placed over the resilient plates proximal to top plate 16$t$ and distal to bottom plate 16$b$. Top and bottom protective layers, 12$t$ and 12$b$, are bonded together at their edges as shown in FIG. 2, to provide protection for the piezoelectric material, plates and padding enclosed therein.

Figure 3:
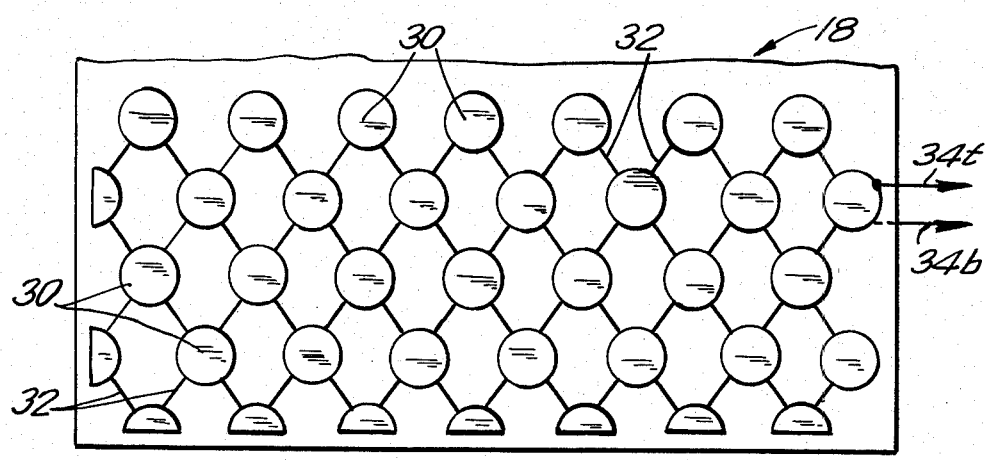
FIG. 3 is a planar view of a metalized surface of the piezoelectric material of the transducer of FIG. 1 showing one electrode configuration.
Figure 4:
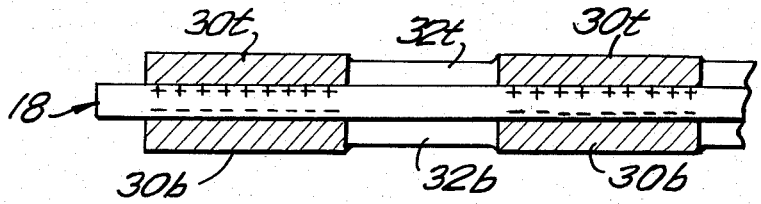
FIG. 4 is a cross-sectional view of the metalized piezoelectric material of FIG. 3.

Metal contacts or electrodes (metallized areas) are attached to both surfaces of piezoelectric material 18 for sensing the induced surface charges which are proportional to the magnitude and direction of the applied force, F, as explained above. In this embodiment, a plurality of metal disc-shaped electrodes 30, as shown in FIGS. 3 and 4, are attached to piezoelectric material 18. The plurality of metal disc electrodes are uniformly spaced-apart from one another over substantially the entire surface area of the piezoelectric material and are arranged in a rows and staggered columns configuration, i.e. a matrix. Each disc is electrically connected to another disc, obliquely or diagonally positioned with respect to it, by electrical leads 32. The electrically interconnected matrix configuration of the metal disc electrodes may be attached, i.e. by vapor deposition, to one surface of the piezoelectric material while the opposite surface has one common electrode or both surfaces may have attached thereto the metal electrode matrix configuration shown in FIG. 3. It is recognized by those skilled in the art that the metal electrodes may be of substantially any shape, i.e. square, triangular, or rectangular, and the configuration or electrode pattern may be different without altering its purpose or function.

FIG. 4 shows the position of the disc electrodes with respect to each other on either side of the piezoelectric material when both surfaces of the material have the above described metal disc electrode configuration. Electrodes 30t on one surface are substantially directly aligned with electrodes 30b on the opposite surface of the piezoelectric material. The electrodes sense or "pick up" the external surface charges (++++ and ————) produced by the displacement of the internal, lattice charges caused by the mechanical deformation of the crystallographic lattice axes of piezoelectric material 18 due to the motion of a mass exerting a force thereon. Electrodes 30t are electrically connected by leads 32t and electrodes 30b are electrically connected by leads 32b. The electrodes only "pick up" the external charges closest to each electrode. The charges at the electrodes produce a signal between output leads 34t and 34b proportional to the magnitude of the changing mechanical forces exerted by the mass on the transducer. Output leads 34t and 34b, are electrically connected to disc electrode configurations on the top and bottom of piezoelectric material 18, respectively, as shown in FIG. 3. The output signal is transmitted via output leads 34t and 34b to monitoring means 38 along cable means 36 as shown in FIG. 1. The monitoring means, including a charge-to-voltage converter, and cable means are collectively defined as electronic circuit means for processing the output signal and displaying cardiac and respiratory activity.

The cardio-respiratory transducer, described above, must be supported by a mattress but may be under the mattress sheet. When a substantially vertical force is applied to transducer 10, as shown in FIG. 1, external charges are formed on the surfaces of the PVDF film which are "picked up" by disc electrodes 30, i.e. electrodes 30t on one surface and electrodes 30b on the opposite surface of piezoelectric material 18 as shown in FIG. 4. The external surface (electrical) charges are produced by the deformation of the crystallographic lattice axes of the PVDF film as the film is stretched horizontally when first and second convex members, 22t and 22b, press against opposite surfaces of the piezoelectric material due to the substantially vertical mechanical force applied to the transducer.

The size of each disc electrode will vary depending upon the size of the patient since, during respiration, the patient's center of gravity will shift producing a transducer output signal in the manner described above. Generally, infants would require disc sizes of from approximately 1.5 to 2 inches in diameter where the space between adjacent discs would be approximately 2 inches. Adults would require disc sizes of from approximately 4 to 5 inches in diameter where the spacing between adjacent discs would be approximately 5 inches.

Figure 5:
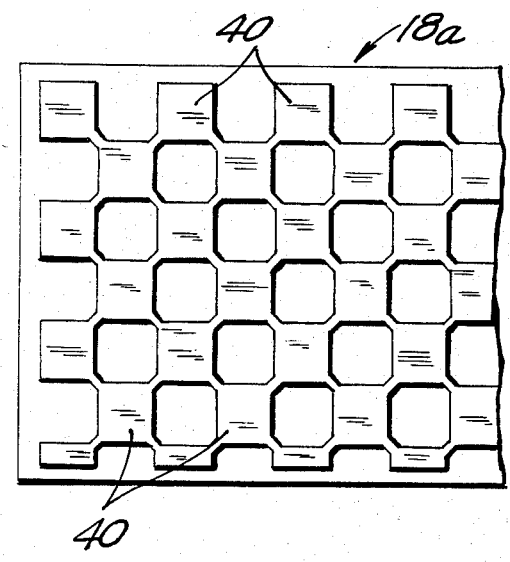
FIG. 5 is a planar view of a metalized surface of the piezoelectric material of the transducer of FIG. 1 showing another electrode configuration.

The disc or first uniformly spaced-apart electrode configuration shown in FIG. 3 is responsive to a patient's cardiac activity (heart beats) and respiratory activity when the patient is lying on the mattress, i.e. on the transducer. However, the electrode configuration shown in FIG. 5 is also capable of detecting horizontal translation of the center of gravity due to respiratory activity as well as substantially vertical displacement due to cardiac activity. Checkerboard or second uniformly spaced-apart electrode configuration 40 provides spaced-apart sensitive and non-sensitive areas for responding to the turning moment produced by a patient's respiratory activity as well as for responding to vertical displacement produced by a patient's cardiac activity. The checkerboard electrode configuration of FIG. 5 is attached to piezoelectric material 18a and each electrode therein is electrically connected to other electrodes and to the electronic circuit means substantially in the manner described above for the disc electrode configuration. When used with infants, each square-shaped electrode in the checkerboard configuration is approximately 50 mm on a side. The spacing between adjacent squares is approximately 50 mm.

Figure 6:
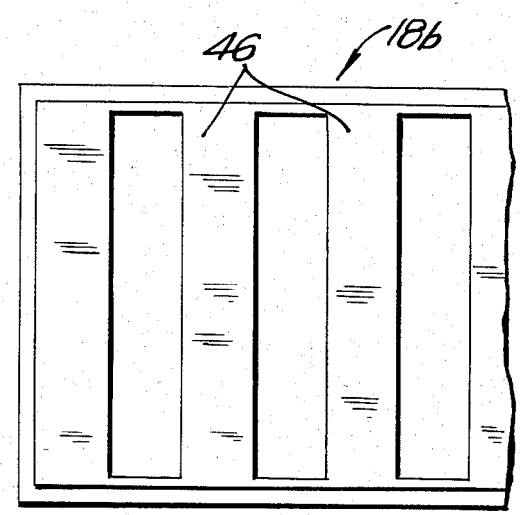
FIG. 6 is a planar view of a metalized surface of the piezoelectric material of the transducer of FIG. 1 showing yet another electrode configuration.

Rectangular or third uniformly spaced-apart electrode configuration 46 is shown in FIG. 6. The rectangular electrode configuration of FIG. 6 is attached to piezoelectric material 18b and each rectangular-shaped electrode therein is electrically connected to other rectangular-shaped electrodes and to the electronic circuit means to form a complete circuit substantially in the manner described above for the first and second uniformly spaced-apart electrode configurations. It would be obvious to one skilled in the art that the electrodes may be shaped and configured in a variety of ways. The configuration in FIG. 6 may be used for adults as well as for children.

For all electrode configurations, the size of each convex member on each plate must be much smaller than the size of each electrode. In the above two embodiments, the size of each convex member is approximately one-quarter ($\frac{1}{4}$) inch in diameter.

Even though the rather stiff PVDF film has a thickness of approximately 28 microns in all cases, the length and width of the sheet-like transducer is not limited except for the practical constraints due to the size of the mattress. The optimal position of the transducer would be between the patient and the mattress, i.e. under the mattress sheets. However, at no time does the transducer come into direct contact with the patient's body. Furthermore, the transducer is not connected to the patient in any way, i.e. as around an arm or a leg.

In the present invention, the "piezoelectric effect" is induced into a PVDF film at a temperature of between approximately 60° to 100° C. while the film is stretched uniaxially up to four times its initial length. The electrodes (disc-shaped, square-shaped, rectangular-shaped, etc.) are then deposited by evaporation on predetermined portions of the surfaces of the piezoelectric material in a predetermined configuration as shown in FIGS. 3, 5, and 6. These steps must be performed before transducer 10 is assembled. To polarize the PDVF film before assembly, a high DC voltage must be applied between the deposited electrode matrices on either side of the PVDF film for approximately one hour at a temperature of approximately 80° to 100° C. If the transducer is assembled with an unpolarized PVDF film, the transducer may be heated and polarized via cable means 36 as shown in FIG. 1. The sensitivity of the sheet-like laminated transducer of the present invention is dependent upon the thickness of the PVDF film and the DC voltage used to polarize it. The dielectric strength of the piezoelectric material is a limiting factor in achieving a high sensitivity. The transducer operates within a 0.1 to 10 Hertz bandwidth and is capable of responding to respiratory activity as well as cardiac activity.

What is claimed is:

1. A laminated, sheet-like transducer for electrical connection connected to electronic circuit means responsive to changing mechanical forces applied to said transducer, comprising:

a top flexible plate including a first surface having a matrix of uniformly spaced-apart first convex members, a bottom flexible plate including a second surface having a matrix of uniformly spaced-apart second convex members aligned with the spaces between said first convex members, an electret made of a synthetic resin polymer sandwiched between said first and second surfaces of said top and bottom plates, said electret producing electrical charges when deformed due to said first and second convex members pressing against and horizontally stretching said electret in response to said changing mechanical forces, and electrodes attached to opposite surfaces of said electret, said electrodes forming a uniformly spaced-apart, electrically interconnected electrode configuration on at least one surface of said electret, said electrodes sensing said electrical charges producing a signal for transmission to said electronic circuit means which is proportional to the magnitude of said changing mechanical forces.

2. The transducer of claim 1 in which top and bottom protective layers enclose said top and bottom flexible plates and said electret, said protective layers being bonded together at the edges thereof.

3. The transducer of claim 2 in which foam padding is provided between said top protective layer and said top flexible plate.

4. The transducer of claim 2 in which said protective layers are vinyl.

5. The transducer of claim 1 in which said electret is made of polyvinylidene fluoride.

6. The transducer of claim 5 in which said polyvinylidene fluoride is approximately 28 microns thick.

7. The transducer of claim 1 in which said uniformly spaced-apart electrodes are disc-shaped.

8. The transducer of claim 7 in which said disc-shaped electrodes are arranged in a rows and staggered columns matrix configuration.

9. The transducer of claim 8 in which each of said disc-shaped electrodes is electrically connected to another of said disc-shaped electrodes obliquely positioned with respect thereto.

10. The transducer of claim 8 in which said matrix configuration of disc-shaped electrodes is attached to at least one surface of said electret by vapor deposition.

11. The transducer of claim 7 in which said disc-shaped electrodes are from approximately 1.5 to 2 inches in diameter.

12. The transducer of claim 11 in which the spacing between adjacent disc-shaped electrodes is approximately 2 inches.

13. The transducer of claim 7 in which said disc-shaped electrodes are from approximately 4 to 5 inches in diameter.

14. The transducer of claim 13 in which the spacing between adjacent disc-shaped electrodes is approximately 5 inches.

15. The transducer of claim 1 in which said uniformly spaced-apart electrodes are square-shaped.

16. The transducer of claim 15 in which said square-shaped electrodes are arranged in a checkerboard configuration.

17. The transducer of claim 15 in which each square-shaped electrode is approximately 50 mm on a side.

18. The transducer of claim 17 in which the spacing between adjacent electrodes is approximately 50 mm.

19. The transducer of claim 1 in which said uniformly spaced-apart electrodes are rectangular-shaped.

20. The transducer of claim 1 in which the diameter of each of said convex members is approximately one-quarter ($\frac{1}{4}$) inch.

21. The transducer of claim 1 in which said transducer operates within a bandwidth of from approximately 0.1 to 10 Hertz.

22. The transducer of claim 1 in which said electret is attached to a deformable support layer.

23. The transducer of claim 22 in which said deformable support layer is plastic.

* * * * *